United States Patent [19]
Fowler et al.

[11] Patent Number: 5,370,672
[45] Date of Patent: Dec. 6, 1994

[54] COMPUTER-CONTROLLED NEUROLOGICAL STIMULATION SYSTEM

[75] Inventors: Kim R. Fowler; Richard B. North, both of Baltimore, Md.

[73] Assignee: The Johns Hopkins University, Baltimore, Md.

[21] Appl. No.: 969,691

[22] Filed: Oct. 30, 1992

[51] Int. Cl.[5] ............................................. A61N 1/32
[52] U.S. Cl. ............................................. 607/58
[58] Field of Search ........................ 607/43, 46, 48, 58, 607/62, 63

[56] References Cited

U.S. PATENT DOCUMENTS

| | | | |
|---|---|---|---|
| 3,880,144 | 4/1975 | Coursin et al. | 128/2.1 B |
| 4,157,087 | 6/1979 | Miller et al. | 128/741 |
| 4,166,452 | 9/1979 | Generales, Jr. | 128/741 |
| 4,305,402 | 12/1981 | Katims | 128/741 |
| 4,655,227 | 4/1987 | Gracovetsky | 128/781 |

OTHER PUBLICATIONS

Author: Kim R. Fowler, Title: Neurological Stimulation System, Date: Apr. 13, 1986, 1 page including drawing.

*Primary Examiner*—Lee S. Cohen
*Assistant Examiner*—Marianne Parker
*Attorney, Agent, or Firm*—Eugene J. Pawlikowski

[57] ABSTRACT

Neurological stimulation alleviates chronic pain and other functional neurologic disorders by delivering electrical impulses to the nervous system of a patient. Within this setting, a computer interface optimizes stimulation with commercially available neurostimulators. The computer and interface, in cooperation with a unique graphics input device, deliver arbitrary and unique paradigms of stimulation. The computer interface provides for efficient patient interaction, optimizes stimulation automatically, and reduces the demands imposed on the time of health care professionals.

1 Claim, 19 Drawing Sheets

FIG. 3A
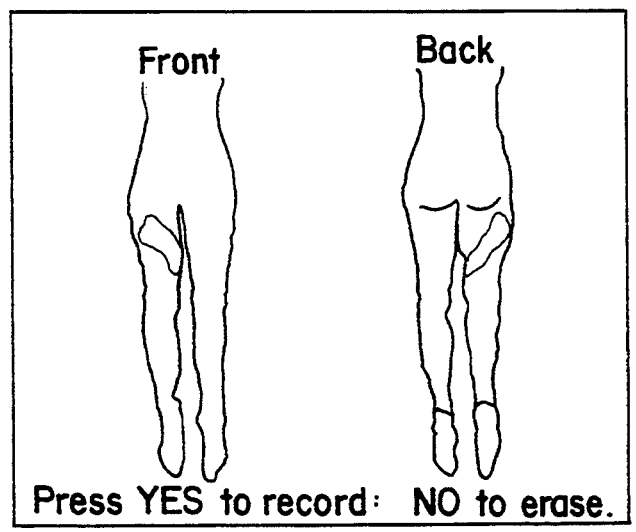
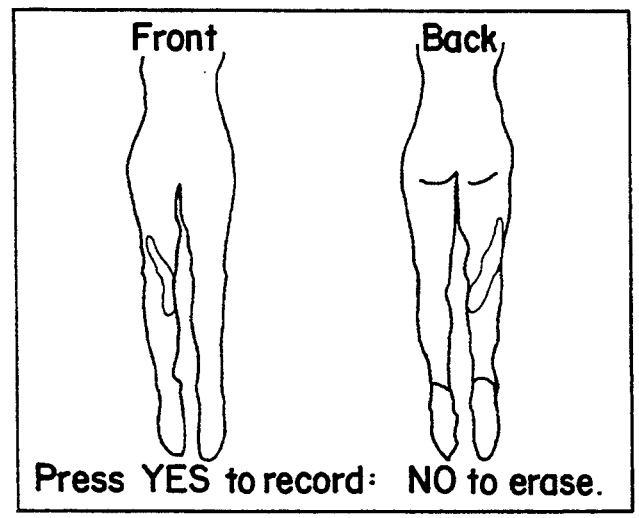
FIG. 3B

FIG. 4A
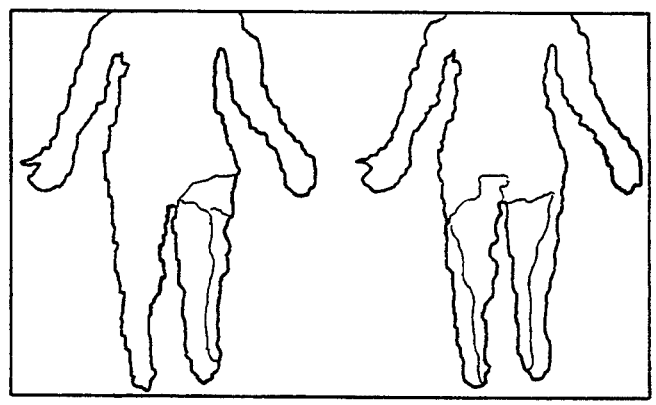
FIG. 4B

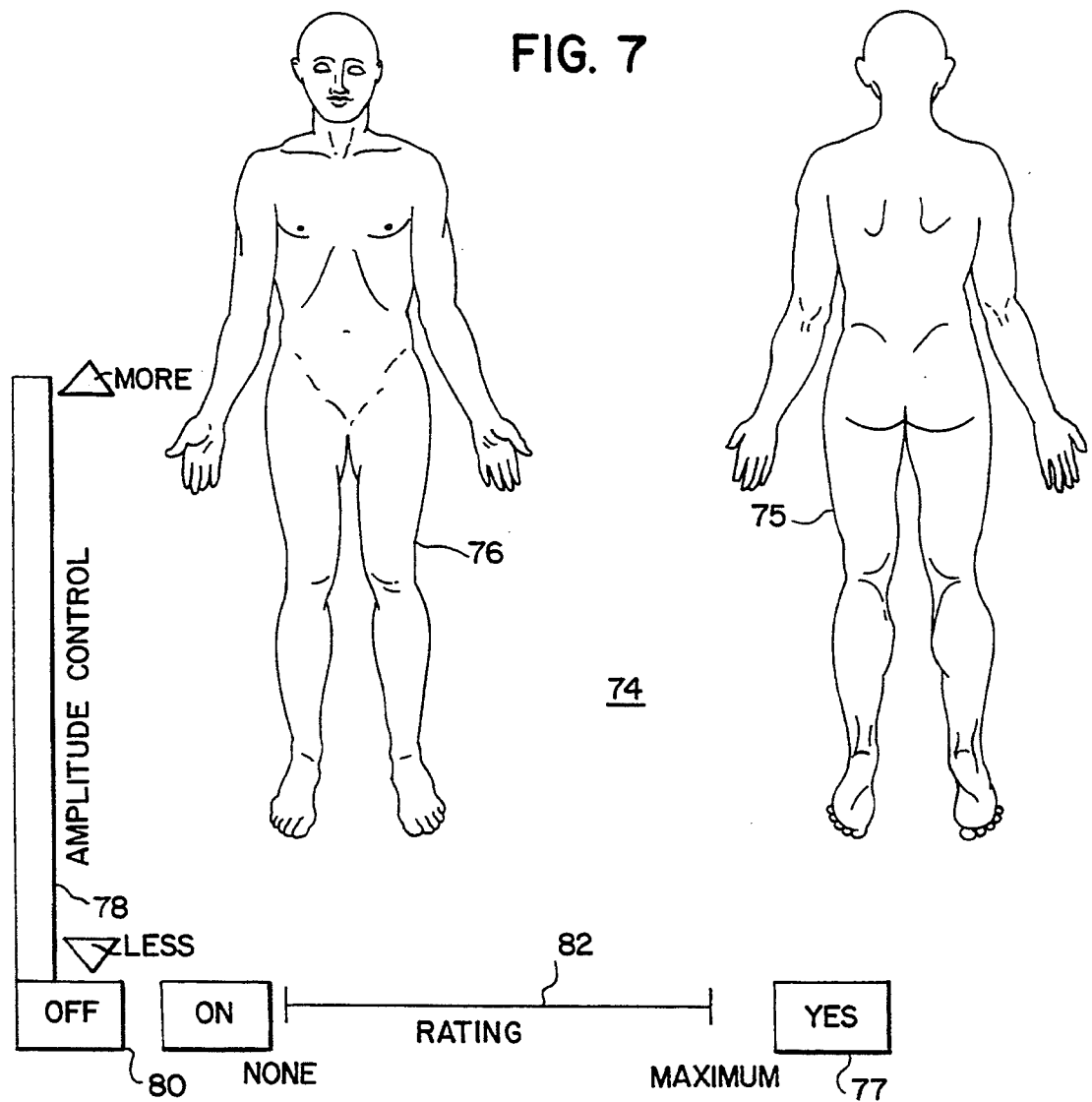

FIG.12

| RAM byte (MSB) | | | | | | | (LSB) |
|---|---|---|---|---|---|---|---|
| 7FH | | | | | | | |
| 2FH | 7F | 7E | 7D | 7C | 7B | 7A | 79 | 78 |
| 2EH | 77 | 76 | 75 | 74 | 73 | 72 | 71 | 70 |
| 2DH | 6F | 6E | 6D | 6C | 6B | 6A | 69 | 68 |
| 2CH | 67 | 66 | 65 | 64 | 63 | 62 | 61 | 60 |
| 2BH | 5F | 5E | 5D | 5C | 5B | 5A | 59 | 58 |
| 2AH | 57 | 56 | 55 | 54 | 53 | 52 | 51 | 50 |
| 29H | 4F | 4E | 4D | 4C | 4B | 4A | 49 | 48 |
| 28H | 47 | 46 | 45 | 44 | 43 | 42 | 41 | 40 |
| 27H | 3F | 3E | 3D | 3C | 3B | 3A | 39 | 38 |
| 26H | 37 | 36 | 35 | 34 | 33 | 32 | 31 | 30 |
| 25H | 2F | 2E | 2D | 2C | 2B | 2A | 29 | 28 |
| 24H | 27 | 26 | 25 | 24 | 23 | 22 | 21 | 20 |
| 23H | 1F | 1E | 1D | 1C | 1B | 1A | 19 | 18 |
| 22H | 17 | 16 | 15 | 14 | 13 | 12 | 11 | 10 |
| 21H | 0F | 0E | 0D | 0C | 0B | 0A | 09 | 08 |
| 20H | 07 | 06 | 05 | 04 | 03 | 02 | 01 | 00 |
| 1FH–18H | Bank 3 | | | | | | |
| 17H–10H | Bank 2 | | | | | | |
| 0FH–08H | Bank 1 | | | | | | |
| 07H–00H | Bank 0 | | | | | | |

| Direct byte address (MSB) | Bit addresses | | | | | | | (LSB) | Hardware register symbol |
|---|---|---|---|---|---|---|---|---|---|
| 0FFH | | | | | | | | | |
| 0F0H | F7 | F6 | F5 | F4 | F3 | F2 | F1 | F0 | B |
| 0E0H | E7 | E6 | E5 | E4 | E3 | E2 | E1 | E0 | ACC |
| 0D0H | D7 | D6 | D5 | D4 | D3 | D2 | D1 | D0 | PSW |
| 0B8H | – | – | – | BC | BB | BA | B9 | B8 | IP |
| 0B0H | B7 | B6 | B5 | B4 | B3 | B2 | B1 | B0 | P3 |
| 0A8H | AF | – | – | AC | AB | AA | A9 | A8 | IE |
| 0A0H | A7 | A6 | A5 | A4 | A3 | A2 | A1 | A0 | P2 |
| 98H | 9F | 9E | 9D | 9C | 9B | 9A | 99 | 98 | SCON |
| 90H | 97 | 96 | 95 | 94 | 93 | 92 | 91 | 90 | P1 |
| 88H | 8F | 8E | 8D | 8C | 8B | 8A | 89 | 88 | TCON |
| 80H | 87 | 86 | 85 | 84 | 83 | 82 | 81 | 80 | P0 |

FIG. 13

| | | | |
|---|---|---|---|
| P1.0 | 1 | 40 | Vcc |
| P1.1 | 2 | 39 | P0.0 |
| P1.2 | 3 | 38 | P0.1 |
| P1.3 | 4 | 37 | P0.2 |
| P1.4 | 5 | 36 | P0.3 |
| P1.5 | 6 | 35 | P0.4 |
| P1.6 | 7 | 34 | P0.5 |
| P1.7 | 8 | 33 | P0.6 |
| RST | 9 | 32 | P0.7 |
| P3.0/RXD | 10 | 31 | $\overline{EA}$ |
| P3.1/TXD | 11 | 30 | ALE |
| P3.2/$\overline{INT0}$ | 12 | 29 | $\overline{PSEN}$ |
| P3.3/$\overline{INT1}$ | 13 | 28 | P2.7 |
| P3.4/T0 | 14 | 27 | P2.6 |
| P3.5/T1 | 15 | 26 | P2.5 |
| P3.6/$\overline{WR}$ | 16 | 25 | P2.4 |
| P3.7/$\overline{RD}$ | 17 | 24 | P2.3 |
| XTAL2 | 18 | 23 | P2.2 |
| XTAL1 | 19 | 22 | P2.1 |
| Vss | 20 | 21 | P2.0 |

COMPUTER-CONTROLLED NEUROLOGICAL STIMULATION SYSTEM

BACKGROUND OF THE INVENTION

A portion of the disclosure of this patent contains material to which a claim of copyright protection is made. The copyright owner has no objection to the facsimile reproduction by anyone of the patent document or the patent disclosure, as it appears in Patent and Trademark Office patent file or records available to the public, but reserves all other rights whatsoever.

FIELD OF THE INVENTION

This application pertains to a neurological stimulation system of the type incorporating a neurostimulator device implanted in a human. Its uses include but are not limited to alleviation of chronic pain by delivering electrical pulses to the nervous system (spinal cord, brain, or peripheral nerve). In particular, the application discloses a unique software and computer interface developed into a new method for the collection of pain drawings as part of a computer-controlled patient-interactive system for use with implanted neurological stimulators.

Implanted electrical stimulation devices have been employed in the management of chronic intractable pain for over twenty years. The most common electrode implantation site has been the dorsal spinal epidural space. Spinal cord stimulation, like peripheral nerve or thalamic stimulation, evokes paresthesias at amplitudes that produce analgesia; the location of these paresthesias varies with electrode location. Empirically, it has proved to be necessary for therapeutic effect that these paresthesias correspond closely to the topography of an individual patient's pain.

The earliest implanted stimulation devices were single-channel, externally powered, radio frequency-coupled systems with monopolar or fixed bipolar spinal electrodes. With recognition of the importance of both patient selection and proper electrode positioning, electrodes that could be placed percutaneously were developed for temporary use and then adapted for chronic implantation. Arrays of multiple electrodes from which an optimum subset could be selected were then introduced; these initially required laminectomy, but then evolved into percutaneous systems. Single-channel implanted electronics necessitated temporary percutaneous test leads connected to an implanted electrode array for determining the configuration of anodes and cathodes to be hard-wired for long-term use. "Multi-channel" programmable systems have been developed, however, to permit the noninvasive selection of anodes and cathodes from an array of outputs after implantation. (Strictly speaking, these are single-channel pulse generators with multiple programmable output gates.) This hardware expedites implantation and minimizes the need for subsequent surgical revision of electrode position.

These technical improvements, however, incur a considerable burden of postoperative adjustment if all available combinations of anodes and cathodes are to be inventoried exhaustively for optimum effect. With four-electrode systems, there are fifty possible electrode combinations; for newer systems with even more electrodes, the number of electrode combinations increases disproportionately. In general, for an array of n electrodes, the total number of unique combinations of anodes and cathodes (including at least one of each) is given by the formula:

$$\sum_{m=2}^{n} \frac{n!\,(2^m - 2)}{(n-m)!\,m!}.$$

For eight electrodes, for example, there are 6050 such combinations.

As the number of available electrodes increases, it becomes increasingly difficult for the physician or assistant to assess the effect of these combinations in a reasonable time. Adjustments to stimulation pulse parameters (amplitude, pulse width, and pulse repetition rate or interpulse interval) compound this problem. The nature of the data to be recorded (topography of stimulation paresthesias as a function of these parameters) requires voluminous graphic or text files. If systematic or scientific study is intended, there are potential difficulties with operator bias, as well as with data acquisition and reduction.

FIG. 1 illustrates the general configuration for delivering electrical stimulation to nervous tissue. The transmitter 10 and implanted receiver 12 are RF coupled by an antenna 14. The transmitter 10, worn externally by the patient 13, encodes the stimulation parameters and the electrode selections, which are then transmitted to the implanted receiver 12 via the antenna. The implant decodes the transmitted information and generates the desired electrical impulses for stimulating electrodes 16 within the spinal column 18. The implant derives power for stimulation of the electrodes by rectification of RF energy generated by the transmitter; a typical implant generally has no other source of power.

Clearly, more electrodes tax the capabilities of the physician and medical staff to inventory the available electrode combinations in a reasonable time. Adjustments to the stimulation's pulse width or frequency compound the problem. Further difficulties arise with operator bias and with data acquisition and reduction.

Optimizing stimulation for pain relief requires a large number of rather trivial, repetitive, and time-consuming tasks. Obviously, automating the process would save time for health professionals and would improve the acquisition and analysis of data. Therefore, we have developed an interface from an IBM personal computer to several commercially available RF transmitters including the Neuromed MNT-4, and the Medtronic SE4 and 3522. The computer, interface, and transmitters which comprise the present invention are collectively called the Neurological Stimulation System (NSS). The NSS controls the associated implanted receiver and electrodes through antennas and RF coupling to stimulate the nervous system. The transmitters are housed in a peripheral enclosure and are connected by a cable to the computer. FIG. 2 shows an earlier version of the NSS in which a stimulation system appears in the form of a peripheral enclosure 20 which incorporates two simple potentiometer controls 22 and 23 and push button control 24. The controls are manipulated by the patient to control stimulation parameters and to record events. A Koalapad graphics tablet 26 external to the peripheral enclosure 20 is also used by the patient and it functions independently of the peripheral enclosure 20 to enter pain drawings and stimulation topography drawings. A standard radio frequency transmitter 28, which includes control circuitry is housed within peripheral enclosure 20. Digital I/O and Analog I/O lines 32 and 34 couple peripheral enclosure 20 to an IBM-XT host computer. Ring antenna 14 couples the transmitter output to the receiver element of the implanted device (not shown).

During operation of the system shown in FIG. 2, the patient interacts with the NSS without direct supervision from the physician. The controls are both easier for the patient to operate and fewer in number than those of a standard commercial transmitter. The Koalapad graphics tablet permits the patient to enter outlines of his painful areas and of the stimulation paresthesias. Visual feedback and instructions are presented to the patient via the computer. A keyboard is required only by the system operator for program initialization and data analysis.

In routine clinical use, the NSS automatically presents a pseudorandom sequence of two-, three-, or four-electrode combinations. In addition, the NSS presents the stimulation with the pulse width and interpulse intervals defined by the physician or operator. The patient responds to the stimulation by controlling the amplitude of the stimulation amplitude control 22 and recording its effects. The patient then outlines the areas of paresthesias on sketches of the body on the tablet and subjectively rates the effect of the stimulation by adjusting the analog rating potentiometer 23. In this manner, the NSS records the optimal settings for the patient's transmitter. FIG. 3 shows the graphical interface of the NSS.

FIG. 4 illustrates the analysis that calculates overlap between areas of pain and stimulation. The calculated overlap, shown as "pain cover" in FIG. 4, is 32%. The patient's rating of pain relief, shown as "pt. cover" in FIG. 4, is 45%. The amplitude of stimulation at the usage level (FIG. 4) is 32% of full scale. The usage level is one of three levels of instruction given to the patient to indicate the amplitude of the self-administered stimulation. The combination of electrode polarities used in this session is "−off+off."

The goals of the stimulator adjustment were to maximize the overlap of stimulation paresthesias with the topography of pain, to minimize extraneous paresthesias outside the topography of pain, and to minimize the associated uncomfortable muscle cramping. Two experiments examined and optimized the overlap of the painful areas with stimulation. In the first experiment, the operation of the NSS and the manual operation of a transmitter were compared to determine the utility of the NSS. The metrics of comparison were the time duration of testing and the number of combinations of electrode polarities that the patient used for pain relief. In the second experiment, and in accordance with the preferred embodiment of the invention, the computer-calculated overlap between the stimulation paresthesias and painful areas as correlated to the patient's estimate of overlap.

The NSS optimized stimulation for each patient through a series of steps. First, each patient ran a tutorial program for instruction in operating the controls and graphics tablet. The NSS then prompted the patient to draw outlines on the graphics tablet to indicate the areas of pain on the sketches of the body. The NSS selected, in random sequence, a combination of polarities for the four electrodes and then generated stimulation at fixed parameters (e.g., pulse widths of 200 μs and repetition rates of 60 pulses/s) while the patient controlled the amplitude. For each combination, the NSS prompted the patient to adjust the amplitude incrementally upward to one of three levels. At each amplitude and for each electrode combination, the patient recorded both an outline of the topography of the paresthesias and a magnitude estimation of the paresthesia's overlap with the topography of the pain. Patients were selected randomly from an ongoing clinical series regardless of prior exposure to computers or perceived aptitude.

To compare patient operation of the NSS, each patient manually adjusted the transmitter under supervised instruction. First, each patient received instructions in using the standard transmitter from a physician's assistant. Then the patient was assisted in testing the stimulation parameters. For each combination of electrode polarities, the assistant recorded verbal descriptions of both the stimulation coverage and the magnitude estimations of the overlap between paresthesias and pain. Following discharge from the hospital, each patient continued to test stimulation parameters so as to optimize pain relief.

While generally satisfactory performance has been realized from programmable neurostimulation devices considerable time is required by a health professional or physician to supervise the adjustment of the transmitter, when selecting the optimum combination of pulse width and pulse repetition rates of the stimulation impulse. The extra time required for patient adjustment of the variables by manipulation of the stimulus and rating potentiometer is also a factor. It has been found that unsupervised testing by patients outside the clinic results in significantly fewer useful combinations being found in comparison with testing by the NSS or a physician's assistant. Since pain relief is directly associated with the overlap of painful areas by the stimulation paresthesias, efforts continue to improve the quantitative analysis of stimulation paresthesias and pain topographics.

SUMMARY OF THE INVENTION

As an alternative to standard manual methods of adjustment the neurological stimulation system allows for more precise correlation of the overlap between the locations of pain and the location of stimulation paresthesias. The system presents a wide variety of stimulus values, which can vary on a pulse-to-pulse basis, in an ordered sequence, at rates beyond the capabilities of manual adjustment, and with less reliance on subjective interpretations and adjustments by the patient. Recording the results of stimulation is automatic, thereby facilitating analysis. Operator bias is reduced by interacting directly with the patient.

A custom interface card in an enclosure contains the circuitry to control the desired transmitter, to communicate serially with a host computer, and to time events accurately. A graphics tablet connected to the host computer permits entry of the locations of perceived stimulation paresthesias as well as the painful areas. Patient input to the system requires only moving a stylus over the graphics tablet. The doctor or assistant initiates a session by calling up the appropriate programs in the computer. The operator commands the host computer via the keyboard to set up files for record keeping and to prepare for the collection and analysis of data. The computer and interface enclosure control the selected transmitter and establish stimulation parameters (frequency, pulse amplitude and width, and electrode combination). The patient interacts via the graphics tablet to adjust the stimulation amplitude, to enter into the computer the areas of pain and paresthesias, and to enter linear analog ratings. Selected electrode combinations afford stimulation paresthesias corresponding best to a patient's reported distribution of pain. After recording graphical data from the patient, the NSS quantitatively analyzes it. The software anneals the raw data that represent outlines around painful areas and stimulation paresthesias by closing the open contours and then by filling the interior of each outline. The software identifies the intersection of each outline with the interior of the body outline, compares the resulting pain and stimulation maps, and identifies the areas of overlap. Overlap is quantified as the ratio of intersection of pain and stimulation maps to the total area of the pain map, and is then tabulated with corresponding amplitude settings and patient estimations of pain relief.

Accordingly, an object of the invention is to provide an improved neurological stimulation device for the relief of chronic, intractable pain.

Another object of the invention in a neurological stimulation device is to centralize on the graphics tablet all inputs from the patient, thus eliminating potentiometers and pushbuttons found in prior art devices.

Still a further object of the invention is automate to the parameter selection process during neurological stimulation of a patient in order to achieve optimum stimulation.

Yet a further object of the invention is to remove operator bias from a recording procedure.

Still another object of the invention is to extend to regions hitherto unattainable novel sequences of stimulation in the course of treatment of chronic, intractable pain.

BRIEF DESCRIPTION OF THE DRAWINGS

FIG. 3 illustrates conventional graphical displays typical of a graphics tablet for recording (3A) outlines of pain entered by a patient and (3B) outlines of stimulation paresthesias as perceived by a patient.

FIGS. 4A and 4B illustrate analysis programmers to determine the degree of overlap of pain by paresthesias.

FIG. 7 illustrates the format selected for the embodiment shown in FIG. 6 to overlay the surface of the graphics tablet.

FIG. 12 illustrates the bit address maps found in the microcontroller of the interface enclosure.

FIG. 13 shows the pin assignments for the 87C51 microcontroller.

DESCRIPTION OF THE PREFERRED EMBODIMENT

Figure 1:
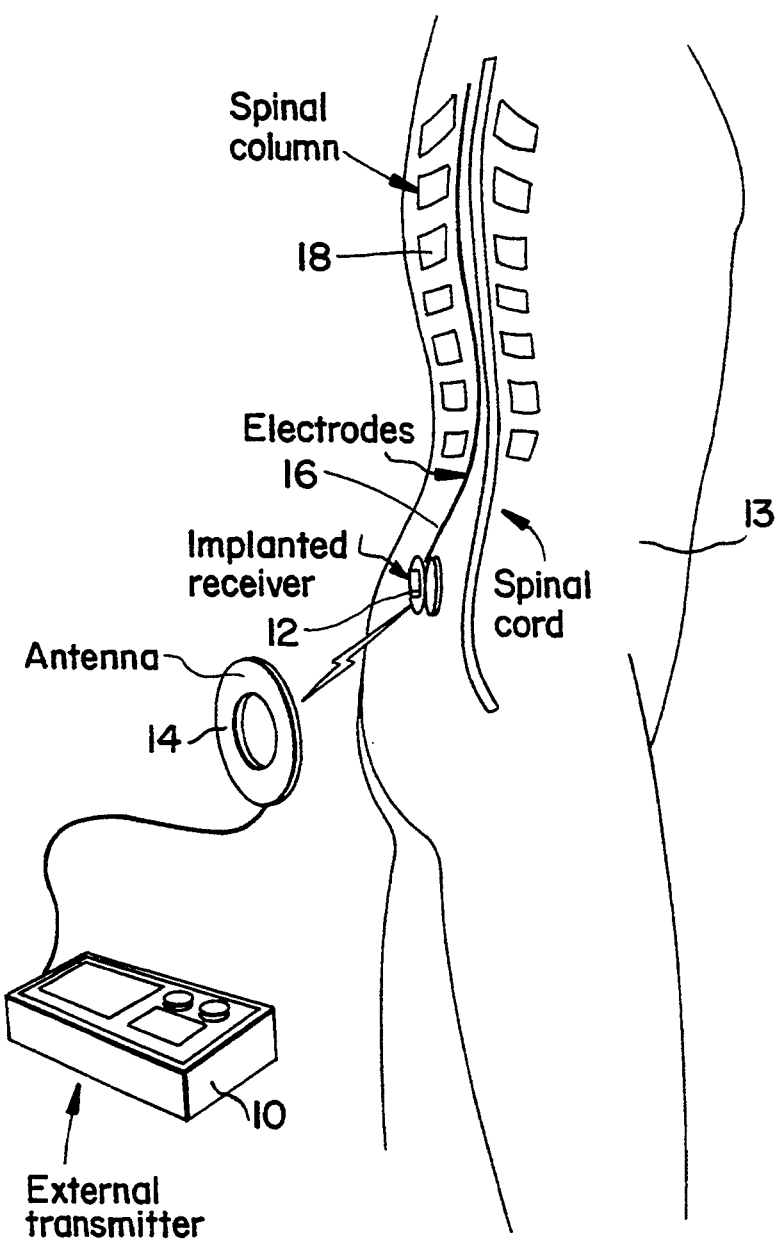
FIG. 1 illustrates a schema for neurological stimulation, as is well known in the art.
Figure 2:
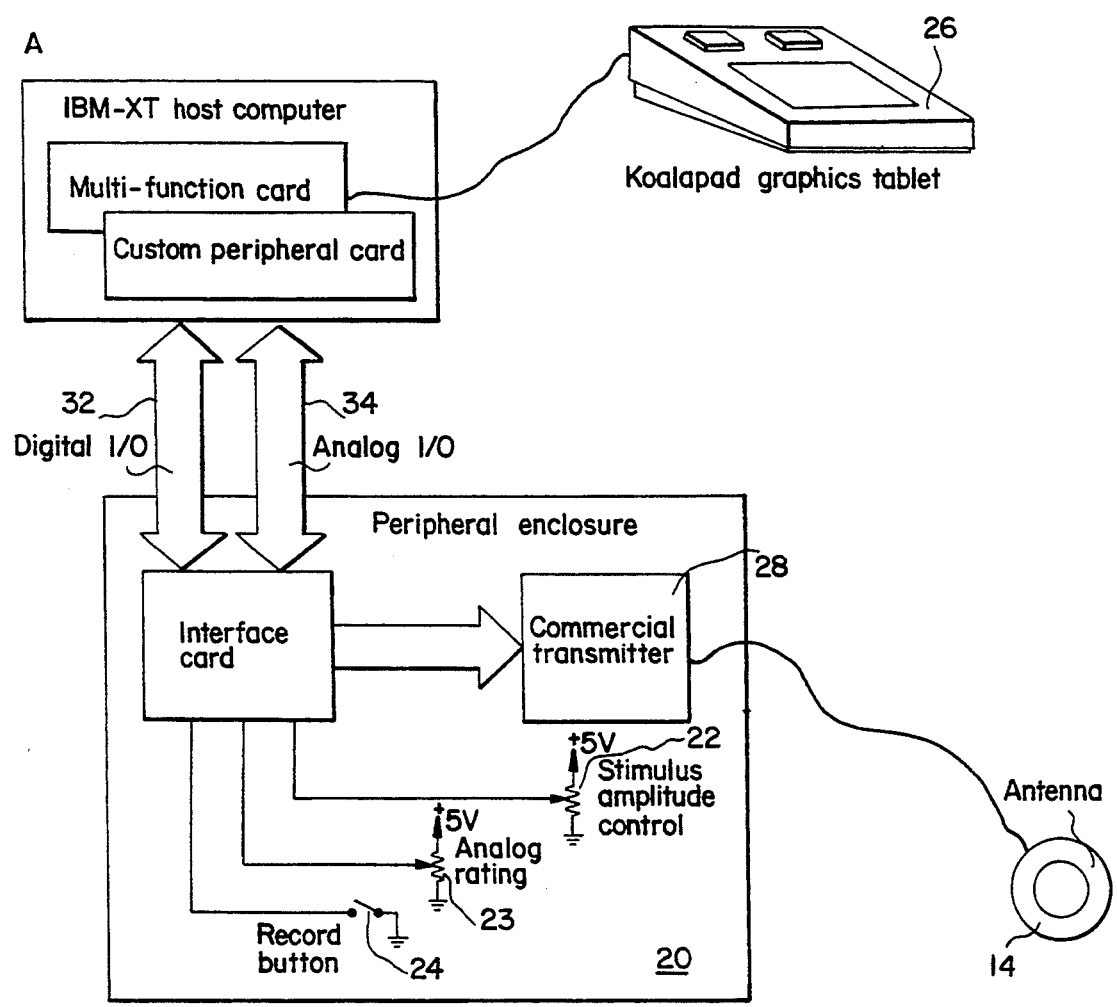
FIG. 2 illustrates a prior art neurological stimulation system with potentiometers and record switch for patient control.
Figure 5:
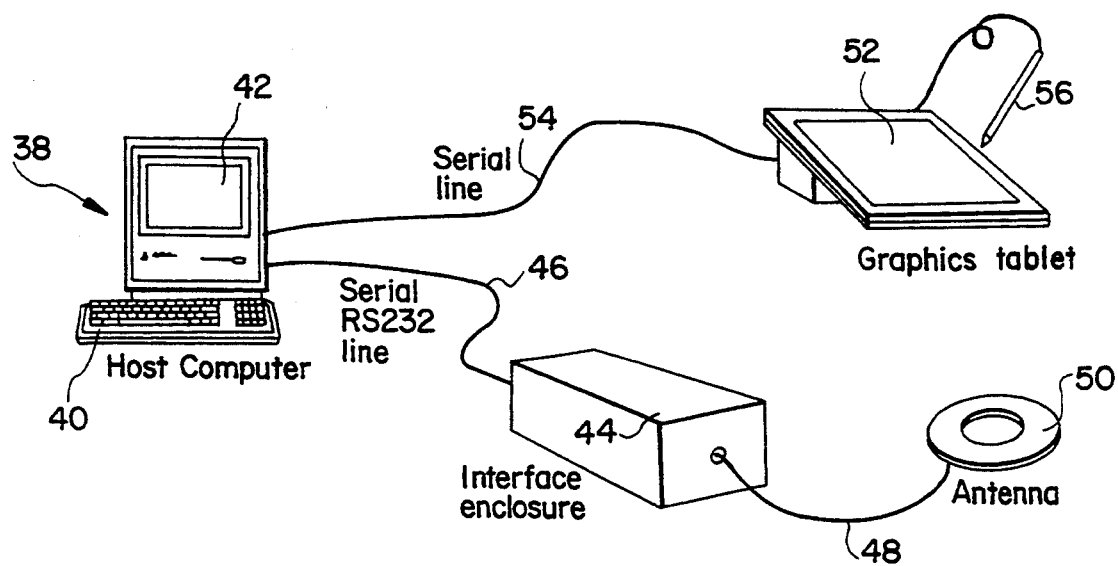
FIG. 5 illustrates the hardware including a graphics tablet for utilizing this invention.

With reference to FIG. 5, the system of this invention comprises a host computer 38 having a keyboard 40 and display screen 42. An interface enclosure 44 is connected to host computer 38 by a serial RS232 line 46, the enclosure 44 having an output line 48 coupled to an antenna 50 of the type routinely associated with implanted hardware for neurological stimulation. A custom interface card (not shown in FIG. 5) located within interface enclosure 44 contains the circuitry, hereinafter to be described, which controls the desired transmitter, communicates serially with host computer 38, and accurately times events. As further shown in FIG. 5, a graphics tablet 52 is connected by a serial line 54 to the host computer 38, which permits entry to the computer 38 of the locations of perceived stimulation paresthesias, as well as the painful areas, when a stylus 56 is manipulated over the table 52 by the patient.

Recognizing that electrode position in a patient undergoing implant treatment is critical to analgesic effect (in that stimulation paresthesias correspond to a patient's painful areas) the ability to adjust the paresthesias noninvasively is invaluable. Formerly, with single-channel devices, electrode position could only be accomplished surgically. The present invention permits selection of stimulating anode(s) and cathode(s) from an array of eight electrodes. The electrode array thus allows adjustments to stimulation in the spatial as well as time domain.

The system shown in FIG. 5 operates in the following manner: the physician or assistant initiates a session with the patient by calling up the appropriate programs in the host computer 38. The operator, via the keyboard 40, commands the host computer to set up files for record keeping and to prepare for the analysis and collection of data. The host computer 38 and interface enclosure 44 control one of several selected transmitters and cause the generation of various stimulation parameters such as frequency, pulse amplitude and width, and electrode combination. The patient at this time is directed via only the graphics tablet 52 to interact with the host computer 38 and the interface enclosure 44 to adjust the stimulation amplitude as necessary and to sketch on the tablet 52 the areas of pain and the areas perceived by the patient to be experiencing paresthesias.

During experimental operation, such as would occur initially in clinical use, the system embodying the invention can optimize routine treatment of patients with implanted spinal electrodes. It is able to select electrode combinations affording simulation paresthesias corresponding best to a patient's reported distribution to pain. "Best", as defined operationally herein, is affording useful coverage by paresthesias, at minimal amplitude by comparison to that causing motor recruitment. For each electrode combination selected, the location of paresthesias may be recorded as a function of pulse amplitude and width allowing descriptive data to be collected in an ongoing basis, just as was formerly done by laborious manual methods.

Figure 6:
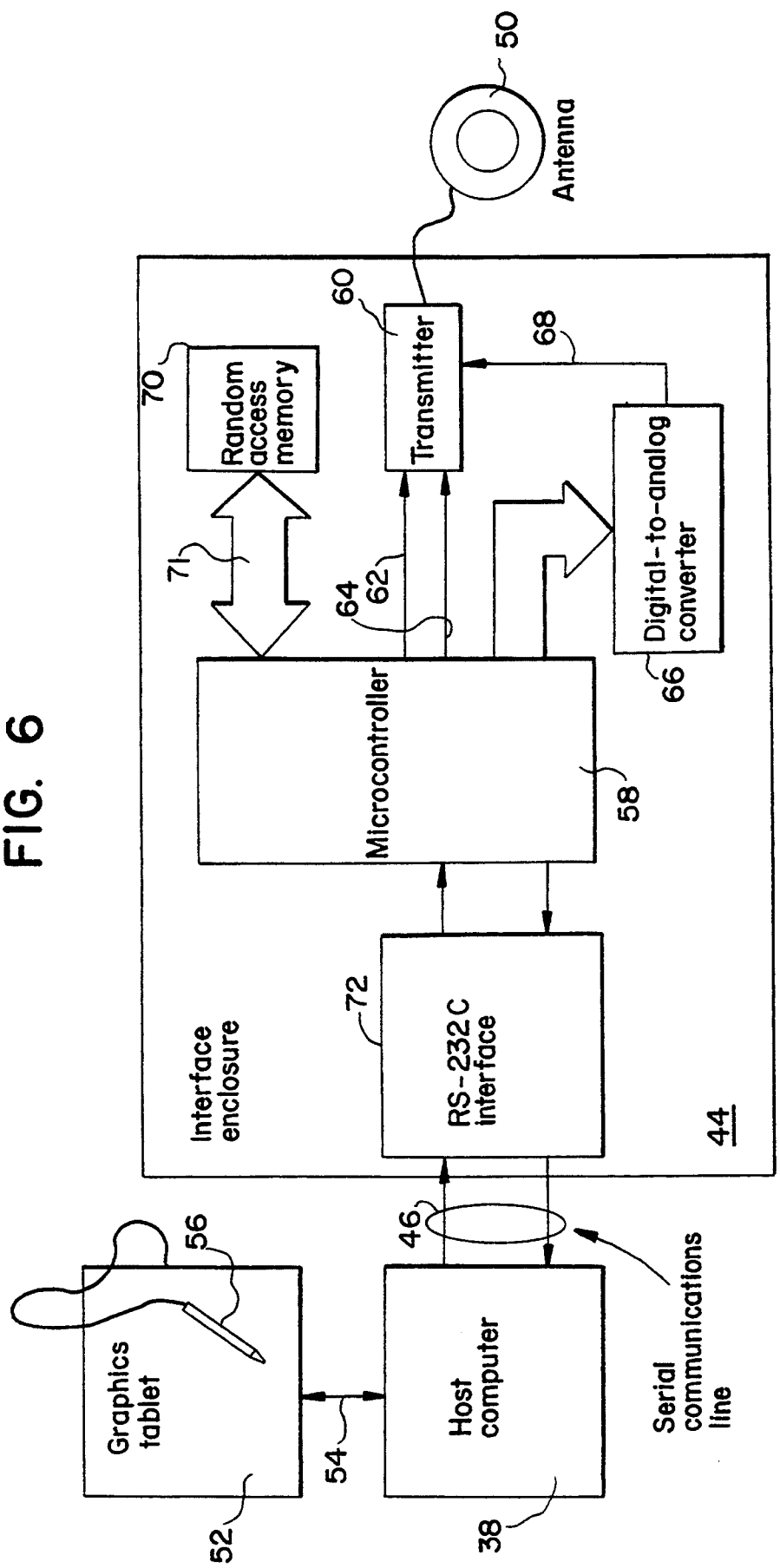
FIG. 6 illustrates in greater detail the neurological stimulation system of the invention expanded to show specific details of the interface enclosure shown in FIG. 5.
Figure 8A:
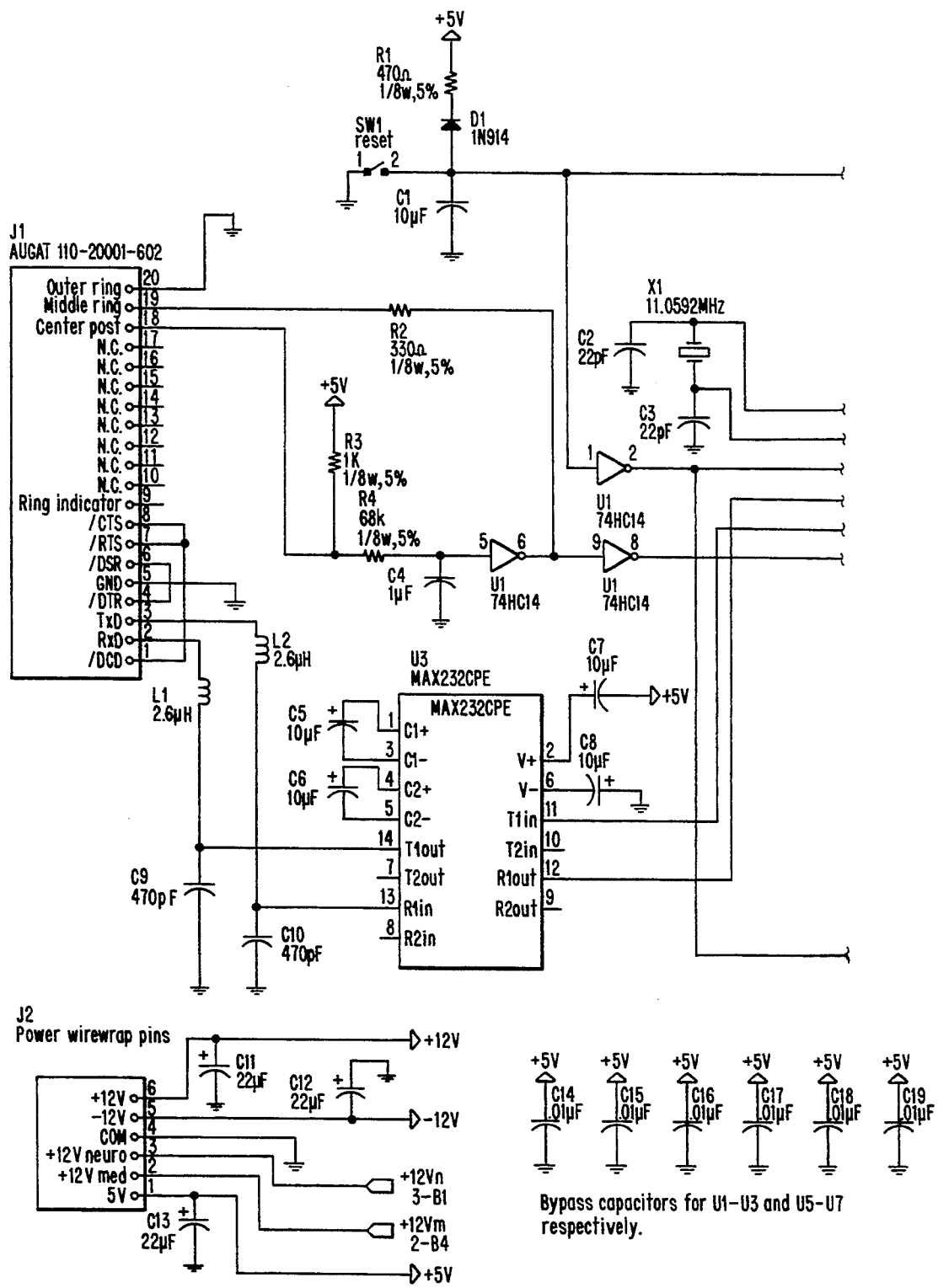
FIGS. 8A, 8B and 9-11 illustrate the microcontroller portion of the interface enclosure shown in the preferred embodiment of the invention as illustrated in FIG. 6.
Figure 8B:
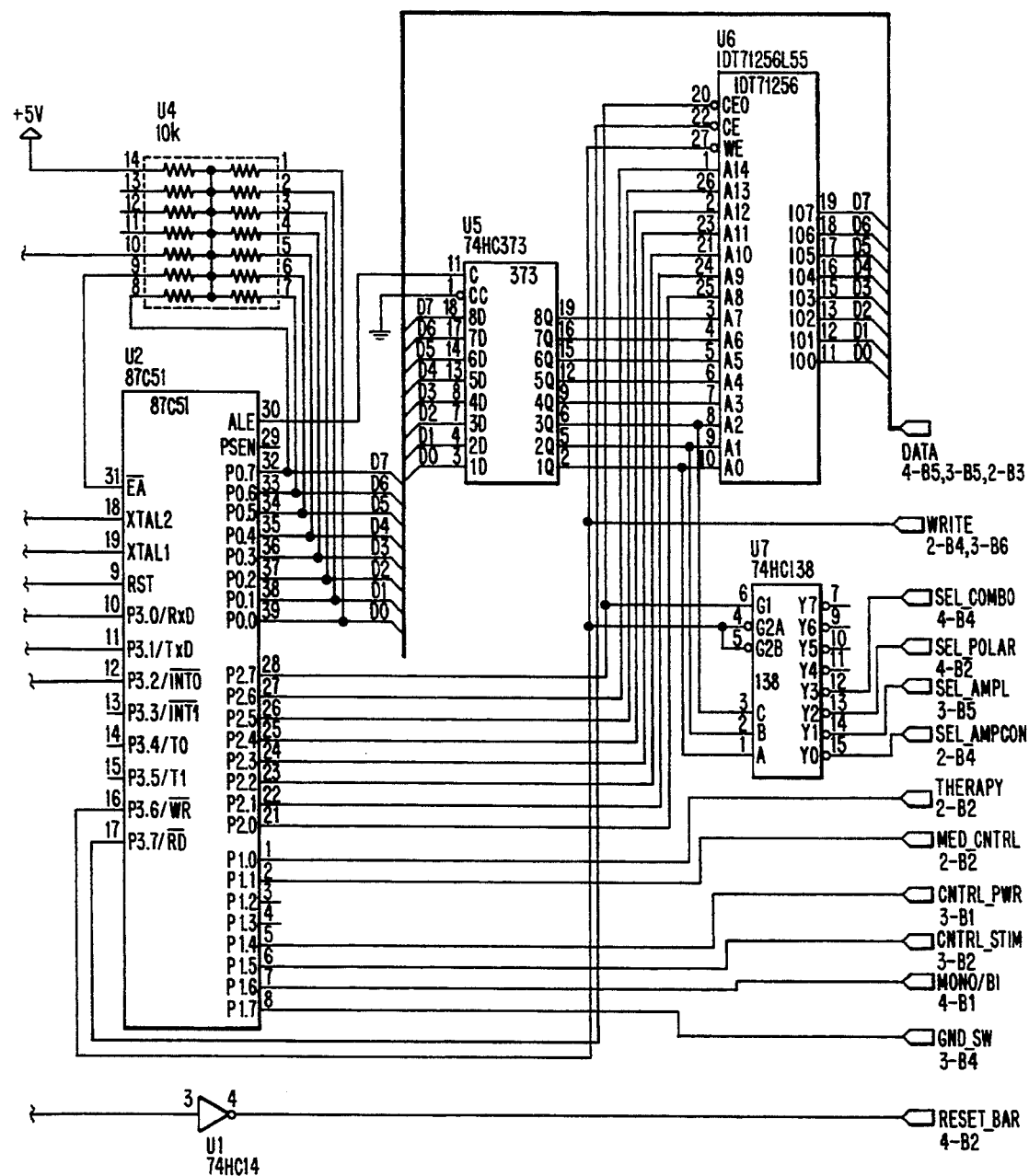
Figure 9:
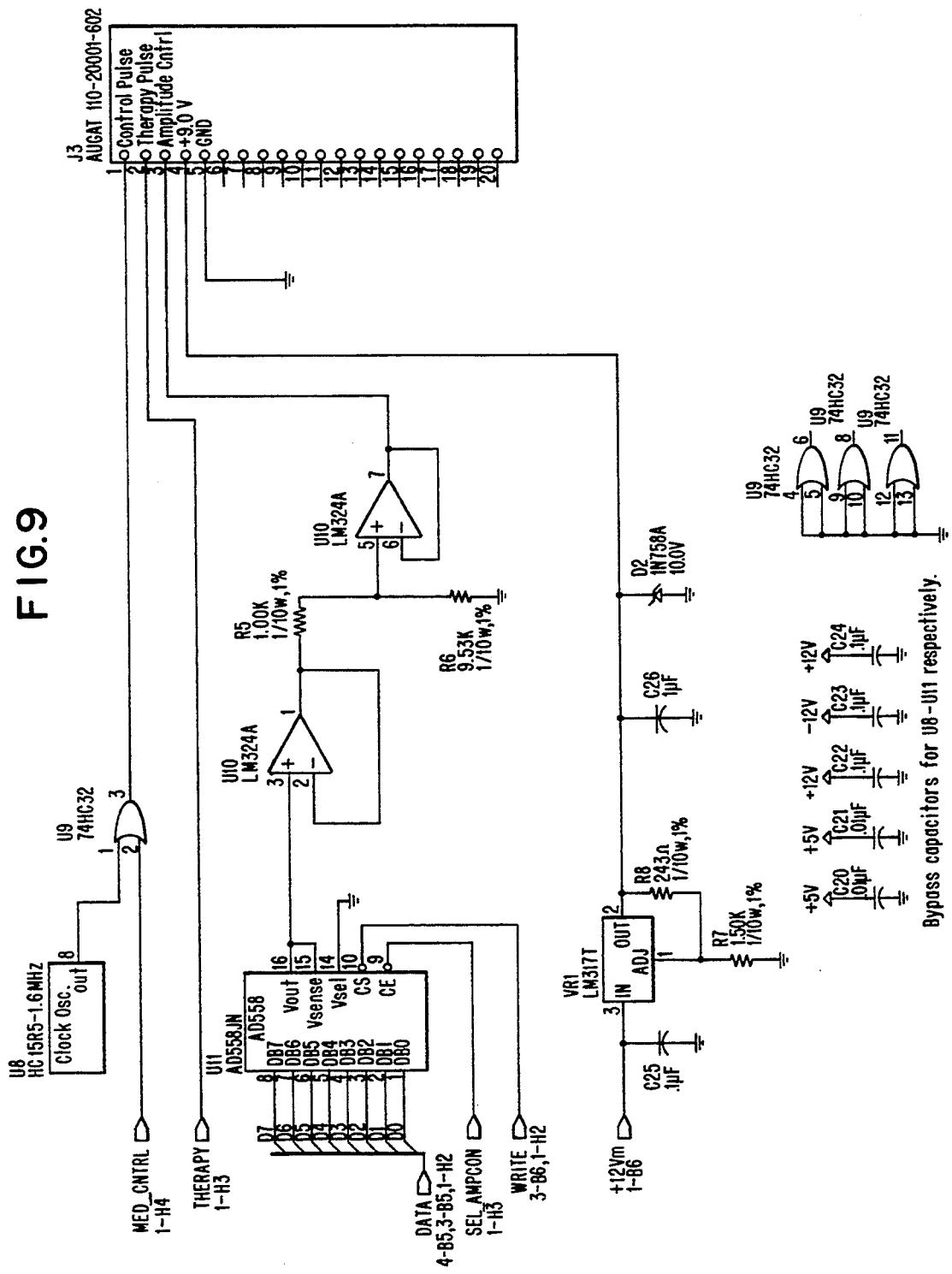
Figure 10:
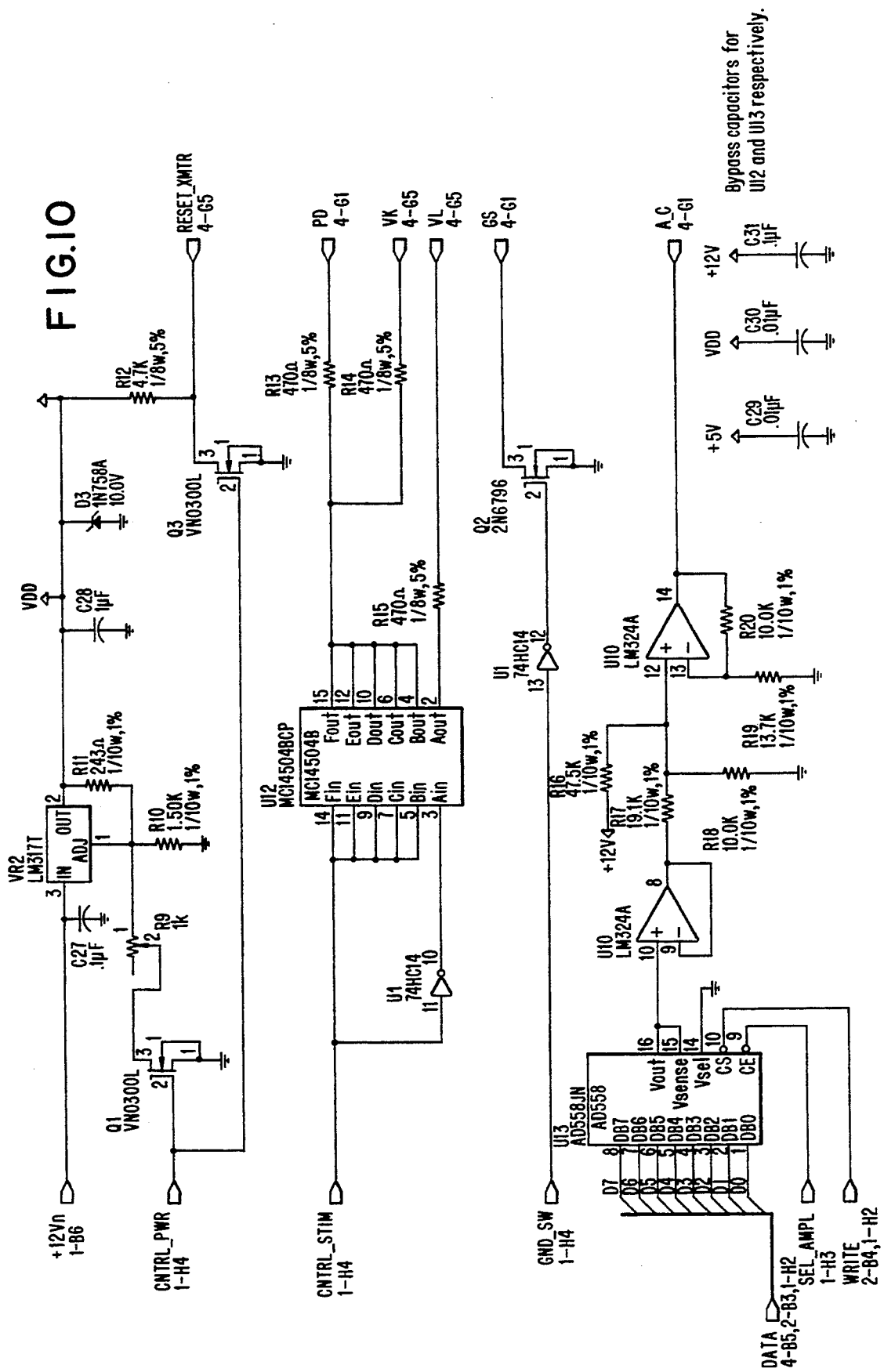
Figure 11:
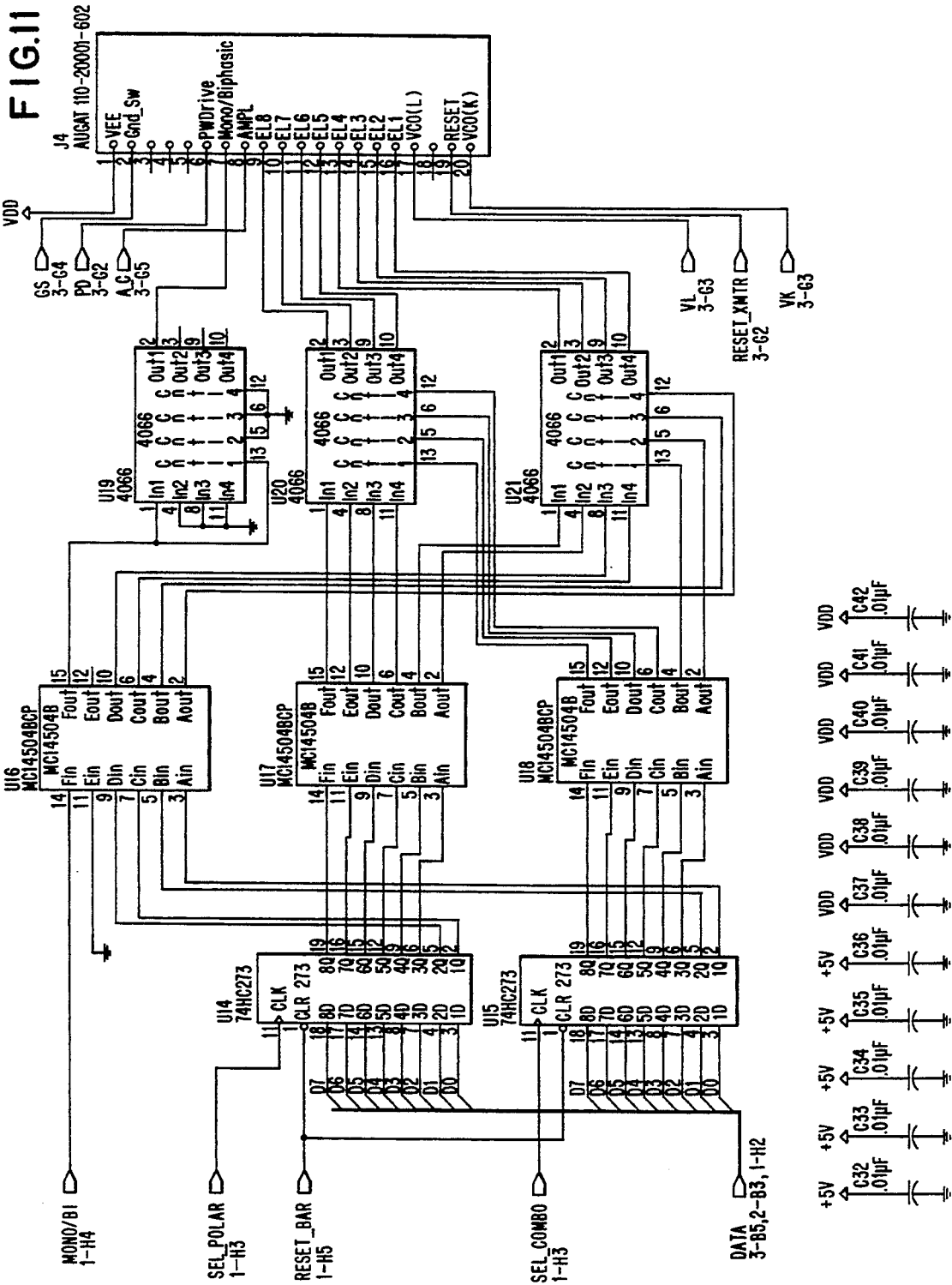

Referring now to FIG. 6 for a description of a more detailed form of the preferred embodiment, the neurological stimulation system has in common with the more generalized embodiment of FIG. 5 the following elements, to which like reference numerals have been assigned: host computer 38, serial RS232 line 46, graphics tablet 52, stylus 56, serial line 54, antenna 50, and interface enclosure 44. More specifically as shown in FIG. 6, the interface enclosure 44 allows for replacement of the manual adjustment knobs and switches of systems associated with the prior art. A microcontroller 58 within the interface enclosure 44 contains a circuit board which accurately times the pulse width and frequency of the stimulation produced by a transmitter 60. The microcontroller generates digital signals on line 62 and 64 which define the parameters of stimulation such as frequency and width of the transmitter pulses. Analog signals by means of a D/A converter 66 which define the amplitude of the pulses are applied to transmitter 60 by means of line 68. A random access memory 70 is coupled to microcontroller 58 by line 71 to read and store data. The circuit board in microcontroller 58 communicates with host computer 38 via a serial RS232C port 72.

During operation of the embodiment illustrated in FIG. 6, host computer 38 provides the high level commands and performs the data analysis. It also interfaces with graphics tablet 52 to accept and record data from the patient. As described above, the patient may outline areas of pain and paresthesias and respond to inquiries by drawing on the tablet. The microcontroller 58 within interface enclosure 44 interfaces with host computer 38 and offloads the realtime control of the transmitter from the host computer. The microcontroller 58 also provides precise timing for the transmitter pulses and modulates the amplitude of stimulation in response to commands from host computer 38. Accordingly, it will be understood from the foregoing description that the host computer completes the multiple functions of recording the areas of perceived pain and the areas of stimulation paresthesias, thus permitting analysis of their interaction. The software in computer 38 also controls and drives the transmitter via the interface enclosure 44 and collects the data following stimulation. The selection of software programs is purely arbitrary but considerable success has been achieved by using programs PAINMAP, PATIENT, and ANALYSIS. PAINMAP and ANALYSIS run standalone on host computer 38 while PATIENT interacts with the transmitter via the computer interface.

In order to better illustrate the operation of the computer-controlled neurological stimulation system of the invention, reference is again made to the graphics tablet 52, one of several commercial versions that allows conversion of two-dimensional information such as a drawing, into a computer readable format. One graphics tablet found suitable for this purpose is the MM®II 1201 graphics tablet manufactured by Summagraphics Corporation, Sixty Silvermine Road, Seymour, Conn. 06483, Copyright 1988–1991. For more information on the MM® II1201 graphics tablet, the following reference is here incorporated by reference: Publication 84-5015-001, November 1991, Summagraphics Corporation.

In the system embodied in FIG. 6, graphics tablet 52 translates the position of stylus 56 on the tablet into digital information concerning a number of variables: pain outline, paresthesias, stimulation amplitude, correspondence of overlap of pain and paresthesias outlines, and command controls. The operating characteristics, functions, and diagnostics are controlled by host computer 38. The surface of tablet 52 is transducer sensitive and is operated by keeping the stylus 56 in proximity with the tablet surface when drawing a pain or paresthesias drawing, changing the stimulation amplitude, or estimating the magnitude of the overlap between paresthesias and pain.

To further assist in understanding the invention, reference is made to FIG. 7. In FIG. 7, there is shown an overlay 74 of clear plastic which, it will be understood, is arranged to cover the surface of graphics tablet 52. When prompted by host computer 38 by a con, hand message the patient, using the stylus 56, sketches on the appropriate part of the anatomical FIGS. 75 and 76 an area which defines the location of the pain presently being experienced by the patient. Upon demand of the host computer 38, the patient, by applying the stylus to the YES sensor area 77 shown to the right of FIG. 7 activates transmitter 60 and D/A converter 66 to excite selected ones of the electrodes 16 implanted in the patient. Upon further prompting by host computer 38, the patient is instructed to adjust the amplitude of the stimulation. This may be done, for example, by applying the stylus to the left of FIG. 7 within the area bounded by the rectangle 78 which has upper and lower limits for demanding either more or less stimulation amplitude or, if preferred, none by placing the stylus 56 in proximity with the OFF sensor area 80. When satisfied with the amplitude adjustment, the patient instructs host computer 38 of comfort with the paresthesias by placing the stylus 56 in proximity with YES sensor area 77. Having ended the period of objective data collection, the remaining elements of the sequence involving the patient include the acts of tracing the area of paresthesias on the selected FIGS. 75 or 76, obeying another prompt from host computer 38 by exciting YES sensor area 77 to indicate satisfaction with the outline of paresthesias, and rating the degree of relief obtained. The function of defining the subjective correspondence of the pain and paresthesias drawings is performed by placing the stylus in proximity with a point on the line sensor area 82. The level of correspondence in the embodiment shown varies between no agreement or overlap of the paresthesias to the topography of pain and maximum agreement.

The controller circuit of interface enclosure 44 is designed around an Intel 87C51 microcontroller whose arrangement is best shown in FIGS. 8, 9, 10, and 11. The chip architecture of the 87C51 microcontroller has four input-output ports, two 16-bit counter-timers, 128 bytes of RAM, and 4K bytes of UVPROM. The 87C51 microcontroller also has two types of memory, i.e, program memory and data memory. The program memory is a read-only memory that contains the software code. The program memory has a capacity for 4K bytes of code internally, and up to 60K bytes externally. The data memory is a read-write memory that may be partitional into registers and random access memory. The data memory has a capacity for 128 bytes of data. Certain portions of the data memory are designated as a special purpose register. FIG. 12 illustrates the address map of the data memory.

An 87C51 microcontroller has a number of special functions as assigned pins. FIG. 13 illustrates the pin assignments of the microcontroller. For more information on the 87C51 microcontroller, the following reference is herein incorporated by reference: Intel "8-Bit Embedded Controller Handbook," 1990, p. 5.1 through 8–103.

The external data memory in the controller allows data to be transferred between interface enclosure 44 and host computer 38. The memory acts as a buffer and allows asynchronous operation in the data transfer. The capacity of the memory is 32K bytes; this capacity is sufficient to store over 3,000 packets of data that define pulse trains for stimulation. A CMOS static RAM, U6 (FIG. 8) implements the external data memory. The capacity of the RAM is 32,768×8 bits. The access time is 55 ns.

The output components are latches, hex level shifters, and digital-to-analog converters that interface with the controller's data bus. The output components, U14 and U15 (FIG. 11) are octal D flipflops. The output components, U11 and U13 (FIGS. 9 and 10, respectively) are digital-to-analog converters (DAC). The output components, U16 through U19 (FIG. 11) are hex level shifters.

The octal D flipflops are 74HC273 integrated circuits. The octal D flipflops latch data from the data bus when the clock input, pin 11, makes a positive edge transition. The clear input, pin 1, is driven by the reset circuitry so that the latch outputs are cleared upon power up.

The hex level shifters are MC14509B integrated circuits. They convert +5 V logic levels to +9 V logic levels for the transmitter.

The digital-to-analog converters are 8-bit AD558 converters from Analog Devices. The DACs latch data from the data bus when the chip enable, CE on pin 9, makes a positive edge transition. The DACs generate analog signals between 0 V and 10.3 V.

Figure 14:
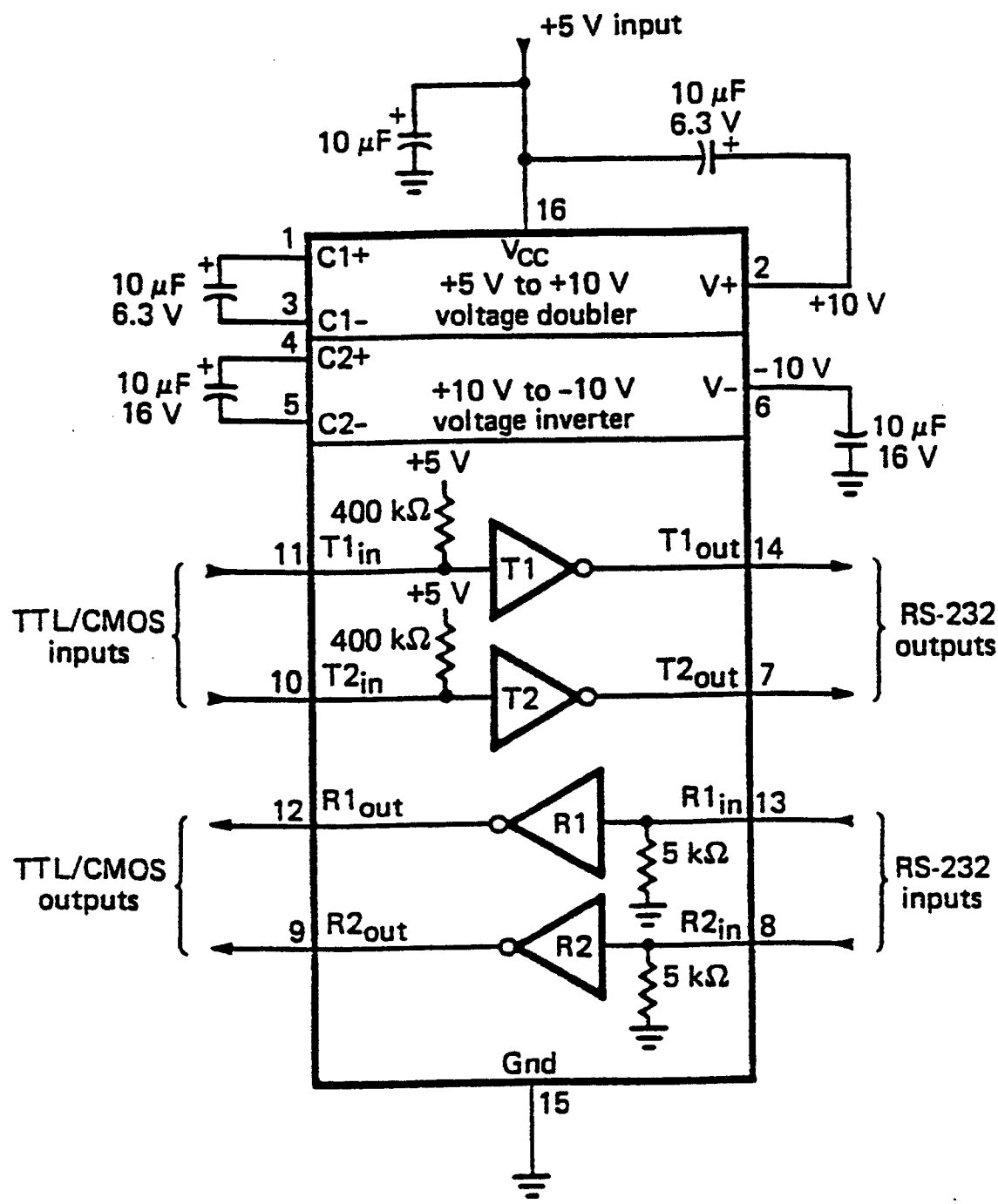
FIG. 14 is a block diagram of the RS232C driver/receivers.

The microcontroller has built-in facilities for serial communications. The driver/receiver component, U3 (FIG. 8), provides the necessary voltage levels for the RS232C communications format. The driver/receiver component operates from +5 V and has internal voltage converters to generate the necessary ±10 V for RS 232C protocol. FIG. 14 illustrates the block diagram of the driver/receiver components, U3, a MAX232.

The static RAM 70 that serves as the external data memory has sufficient timing margin to read and store data. The microcontroller, U2 (FIG. 8) generates an address latch enable signal (ALE) that clocks the multiplexed, LSB address into the octal transparent latch, U5 (FIG. 8), from PO. Simultaneously the MSB address appears at port 2. After setting up the address, a read ($\overline{RM}$) or write ($\overline{WR}$) strobe from the microcontroller determines the data flow from the memory, U6 (FIG. 7). The timing diagrams in FIGS. 15, 16 and 17 are for a 12 MHz microcontroller.

Figure 15:
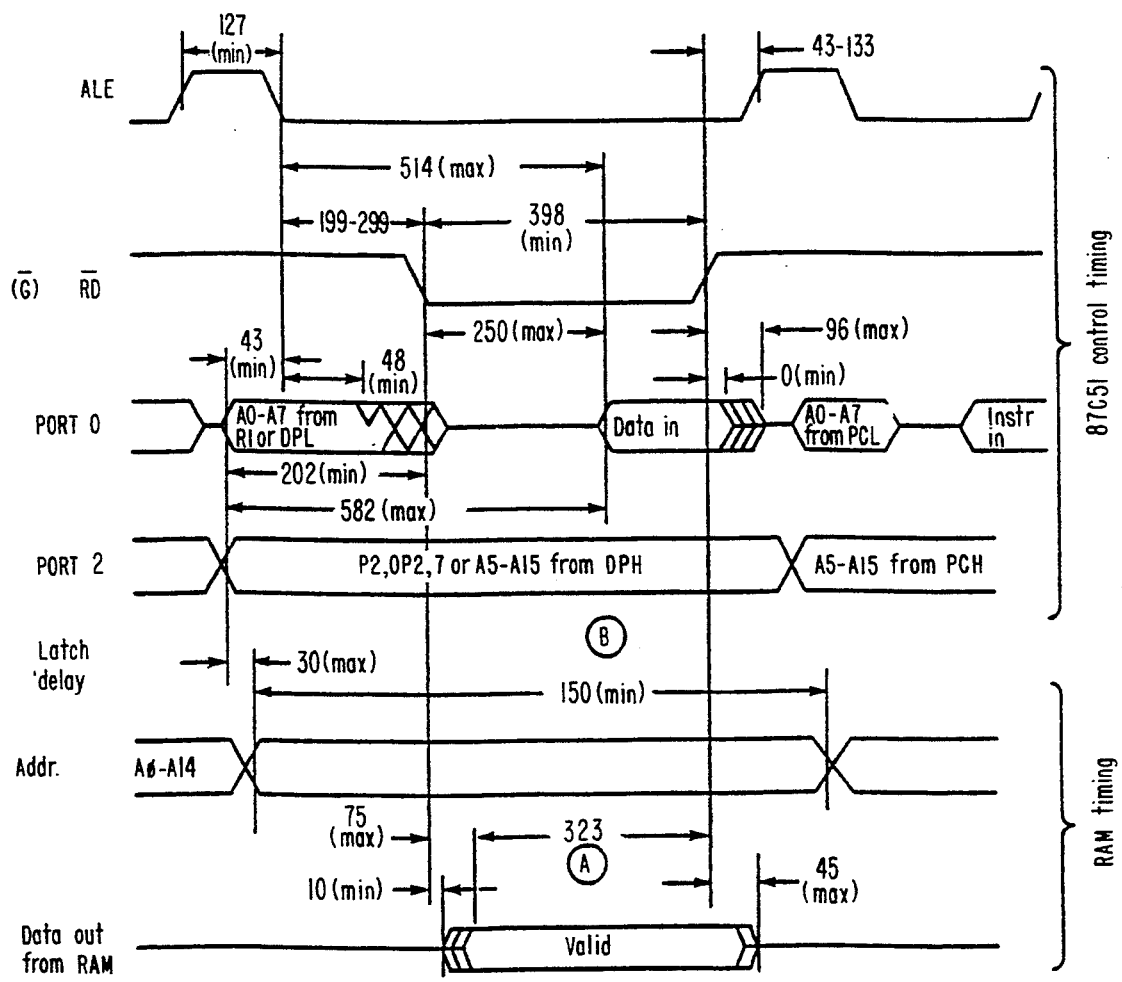
FIG. 15 shows the read timing of 32K×8 random access memory for a 12 MHz microcontroller.

FIG. 15 illustrates the timing of the read operation. The microcontroller reads data from the memory once both the LSB address is latched in U5 and the memory, U6, is enabled by bit P2.7. The negative edge of the read strobe, ($\overline{RD}$), initiates data access from the RAM. The data are valid within 75 nS; this gives an access margin of 175 nS since the data are sampled 250 nS after the negative edge of the read strobe.

Figure 16:
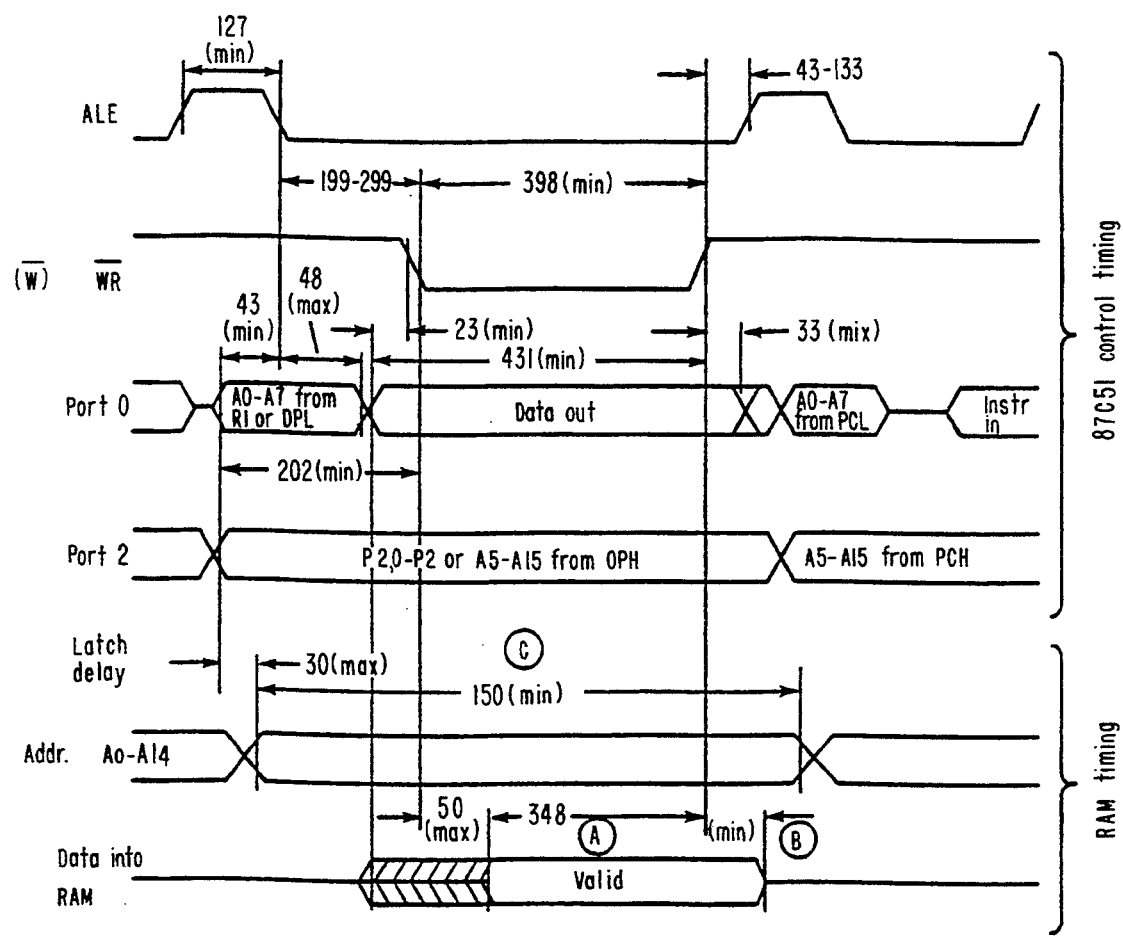
FIG. 16 illustrates the write timing of 32K×8 random access for a 12 MHz microcontroller.
Figure 17:
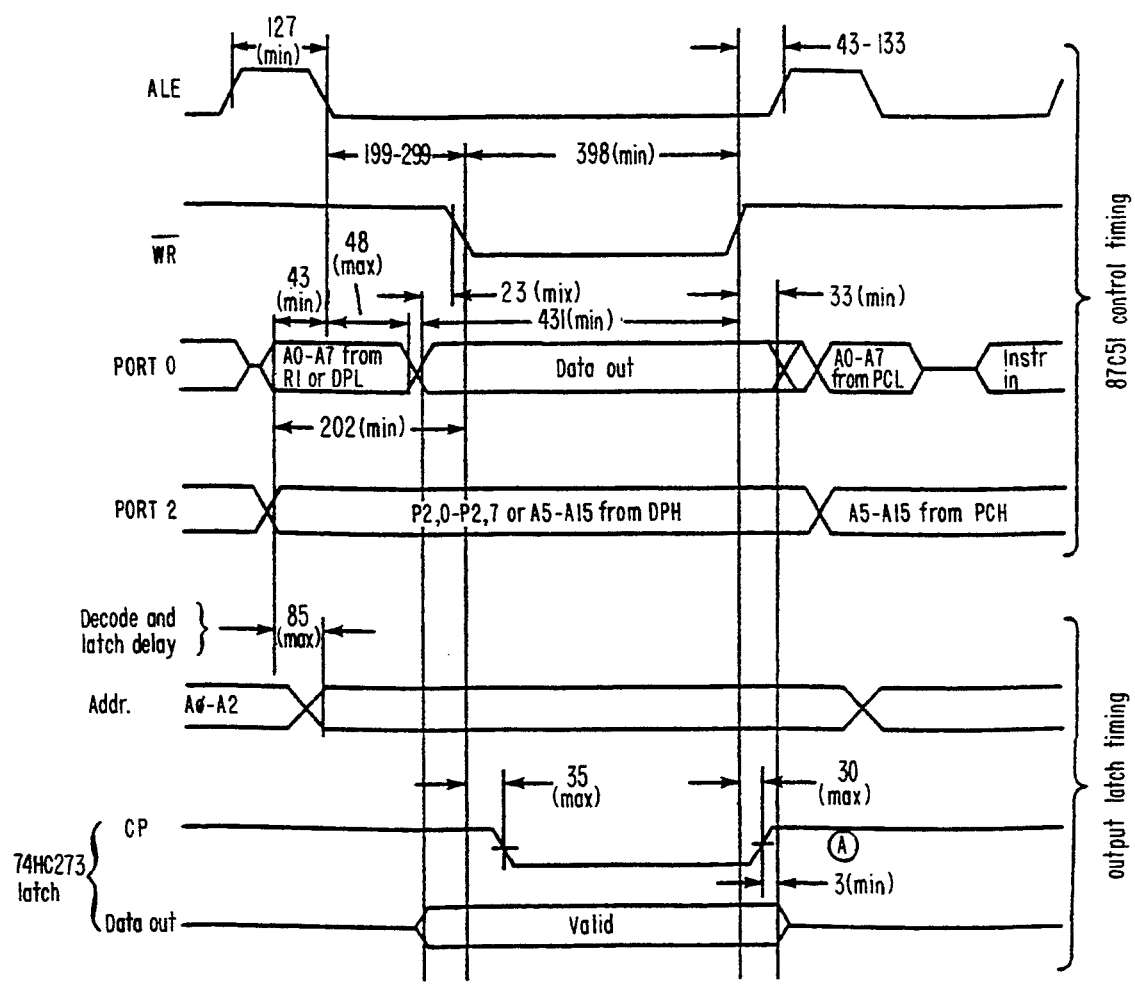
FIG. 17 shows the timing of the output latches.

FIG. 16 illustrates the timing of the write operation. The microcontroller stores data into the memory once both the LSB address is latched in U5 and the memory, U6, is enabled by bit P2.7. The negative edge of the write strobe, ($\overline{WR}$), initiates data storage in the RAM. The data are valid for 348 nS before the positive edge of the write strobe; this gives a set up margin of 298 nS.

The data are held for 33 nS, giving a hold time margin of 28 nS.

FIG. 17 illustrates the timing of the output latches. The output latches have sufficient timing margin to communicate with the transmitter. The 87C51 microcontroller, U2, generates an address latch enable (ALE) that clocks the multiplexed LSB address into the octal transparent latch, U5, from port 0. Simultaneously the MSB address appears on port 2. An active high level on bit P2.7 enables the address decoder, U10. After this action, a write ($\overline{WR}$) strobe activates data transfer with the latches. The rising edge of the write strobe, ($\overline{WR}$), clocks the data from the bus into the output latches with a maximum propagation delay of 30 nS. This leaves a hold time margin of 3 nS as a worst case. The maximum hold time required by the latch is 0 ns.

Figure 18:
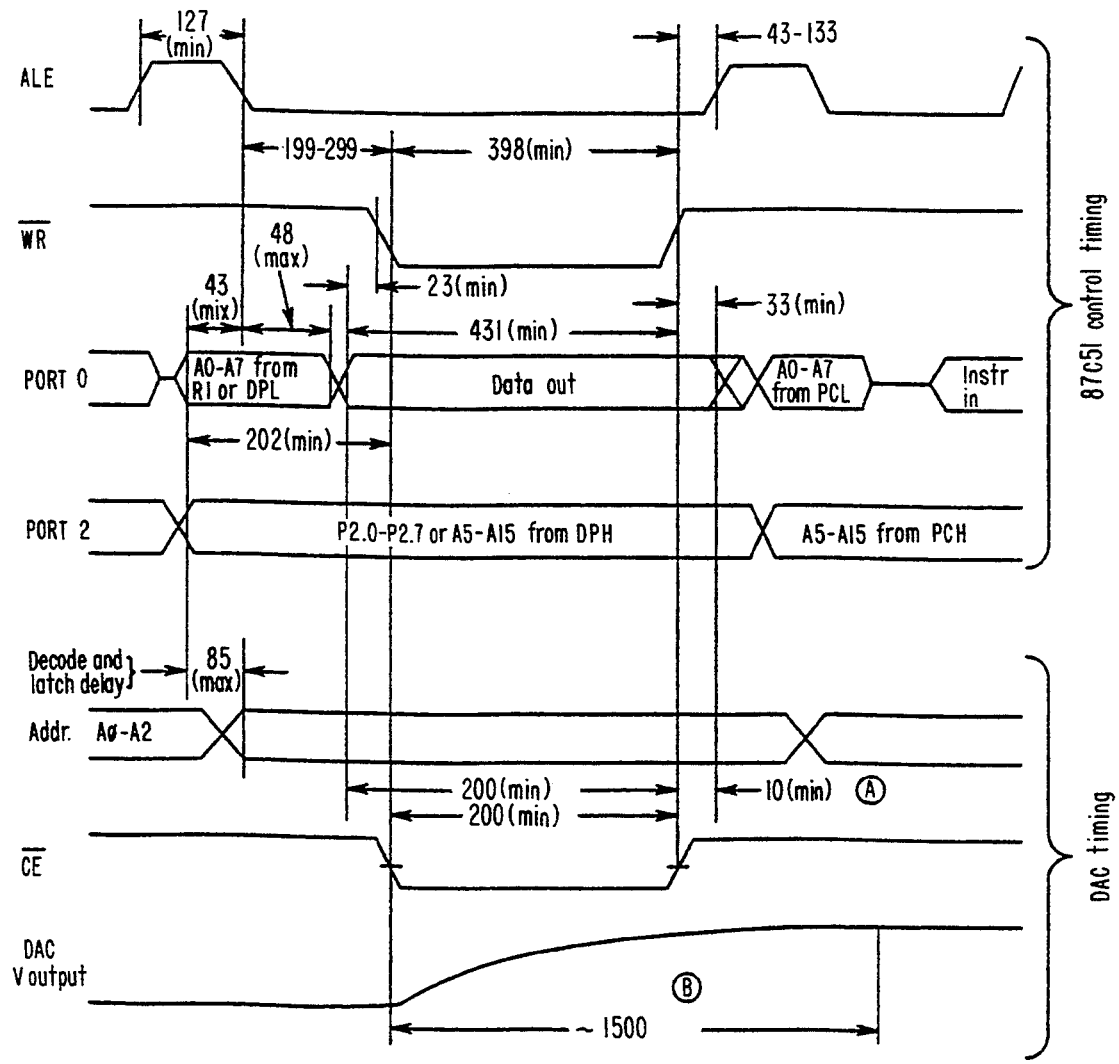
FIG. 18 shows the timing of the digital-to-analog converters.

FIG. 18 illustrates the timing of the DACs. The digital-to-analog converters operate similar to the output latches. The microcontroller latches the LSB address into U5 and presents the MSB address on port 2. An active high level on bit P2.7 enables U10 with decodes the MSB address to select a DAC. The falling edge of the write strobe, ($\overline{WR}$), allows data to be set up in the AC and the rising edge latches the data. The data are held for 33 ns, giving a hold time margin of 23 ns. The full scale output to a step input takes about 1.5 μs to settle to within ½ LSB.

The RS232 interface 72 shown in FIG. 6 has a special format that is not TTL-compatible. The logic levels range between +25 V and −25 V. An RS232 receiver will interpret a voltage more negative than −3 V as a logic 1 and a voltage more positive than +3 V as a logic 0. RS232C transmitters are specified to output a voltage more negative than −5 V for a logic 1 and more positive than +5 for a logic 0. In this way 2 V of noise immunity is guaranteed. Table 1 illustrates some of the RS232C specifications.

TABLE 1

| Parameter | RS232C format Specification |
|---|---|
| Frequency (max) | 20 kbaud/50 ft |
| Logic levels | |
| 0 | >+3 to +25 V |
| 1 | <−3 to −25 V |
| Input impedance | 3–7 kΩ and 2500 pF |
| Output impedance | — |
| Short circuit current | 500 mA |
| Output-slew rate | 30 V/μs |
| Receiver input voltage range | ±15 V |
| Maximum voltage applied to driver output | ±25 V |

The detailed computer program listings for carrying out the data processing steps described in this application are set forth in the following Appendices A–C.

Appendix A contains the driver subroutines to determine the active transmitter, when the choice of one of several transmitters exists.

Appendix B contains the firmware subroutine which is the main code for the interface enclosure. The program is Intel 8051 instruction set code.

Appendix C contains the batch files for assembly, linking and printing.

From the foregoing description it can be seen that the neurostimulation system of the present invention comprises two functional subsystems, a transmitter and an implanted receiver. The transmitter generates the stimulus parameters of frequency, duration, and amplitude of the pulses and the polarity of each electrode. The transmitter encodes pulse parameters via amplitude modulation of a radio frequency (RF) carrier signal. The implanted receiver decodes the RF signal, selects the desired electrode polarities, and generates the desired stimulation. The radio frequency coupling between the transmitter and receiver allows a noninvasive interface. Simply turning off the transmitter or deflecting the antenna from the implant will stop stimulation by the receiver.

The host computer records the area of perceived pain and the areas of stimulation paresthesias, permitting analysis of their interaction. The host software controls and drives the transmitter via the interface enclosure. After the operator has set up and has initiated a file generation request, the patient will enter outlines of painful areas on the graphics tablet. These results are stored for later retrieval and analysis. The operator thereafter enters a program which selects a transmitter to match the patient's implanted receiver; the stimulation parameters of frequency and pulse width are then also selected. Following this the operator selects the general presentation of electrodes (pairs, triples, quadruples, or all possible combinations). The computer randomly orders the presentation of the electrode combinations. At this point the program begins the stimulation and data collection phase. The program instructs the patient to adjust the stimulation amplitude, via the stylus, to any of several levels; perceptual, comfortable (usage), bilateral (both sides of body) or uncomfortable (motor recruitment). These levels are recorded, along with the patient's perceived paresthesias. Finally, the patient enters outlines of the paresthesias on the graphics pad. These results are stored in the disk files for later retrieval.

The recorded maps of pain and paresthesias are then displayed sequentially. Simultaneously the electrode polarities, stimulation level, and the psychophysical levels are displayed.

Although not described herein, adaptation of commercially available "per notebook" computer technology, combining the graphics tablet input with the display screen, is within the scope of the invention. Displays on the pen notebook would take the place of the graphics tablet overlay.

The above and other features of the present invention are illustrative only of preferred embodiments of the present invention, and a variety of modifications and changes may be made therein without departing from the intended scope of the invention.

What is claimed is:

1. A system for collecting and analyzing pain drawings in a computer-controlled neurological stimulation system for use with implanted neurological stimulators for relieving chronic, intractable pain in a patient by optimizing pulses from a transmitter inductively coupled by an antenna to a receiver portion of said stimulators comprising:

a host computer for driving said transmitter to produce output pulses of variable frequency, pulse width, and amplitude;

a tablet;

a graphics input device coupled to said host computer and having a stylus means movable relative to a writing surface of said tablet for generating digital information conveyed to said computer;

said stylus means being responsive to movement by the patient to make a topographical sketch of the pain being experienced, outline a topography of paresthesias in response to said transmitter pulses, and adjust the amplitude of said transmitter pulses;

correspondence indicating means on said graphics input device for indicating overlap of stimulation paresthesias with the topographical sketch of pain;

an interface enclosure;

an interface within said interface enclosure;

said interface enclosure further including microcontroller means operably coupled to said computer through said interface for timing the transmitter pulses and modulating the amplitude of stimulation in response to commands from said computer, for said interface enclosure further including a digital-to-analog converter connected to said microcontroller means and defining the amplitude of the pulses supplied by said transmitter to said antenna;

means for connecting said host computer to said interface enclosure;

an overlay applied to cover the writing surface of said tablet;

said overlay containing anatomical figures on which the patient sketches topographical drawings of perceived pain and paresthesias sensations; and said correspondence indicating means including a line sensor area on said overlay engageable by said stylus means for indicating a level of correspondence which varies between no overlap of the paresthesias to the topography of pain and maximum overlap.

* * * * *